(12) United States Patent
Lillard et al.

(10) Patent No.: US 8,097,250 B2
(45) Date of Patent: Jan. 17, 2012

(54) ANTI-CHEMOKINE AND ASSOCIATED RECEPTORS ANTIBODIES FOR INHIBITION OF GROWTH OF NEOPLASMS

(75) Inventors: James W. Lillard, Smyrna, GA (US); Shailesh Singh, Atlanta, GA (US); Jonathan K. Stiles, Powder Springs, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

(21) Appl. No.: 12/967,273

(22) Filed: Dec. 14, 2010

(65) Prior Publication Data
US 2011/0081406 A1  Apr. 7, 2011

Related U.S. Application Data

(63) Continuation of application No. 10/712,398, filed on Nov. 14, 2003, now Pat. No. 7,919,083.

(60) Provisional application No. 60/426,347, filed on Nov. 15, 2002.

(51) Int. Cl.
*A61K 39/395* (2006.01)

(52) U.S. Cl. .................. 424/130.1; 424/141.1

(58) Field of Classification Search .............. None
See application file for complete search history.

(56) References Cited

U.S. PATENT DOCUMENTS

| 4,818,542 A | 4/1989 | DeLuca et al. |
| 5,530,101 A | 6/1996 | Queen et al. |
| 6,936,248 B1 | 8/2005 | Andrew et al. |

FOREIGN PATENT DOCUMENTS

| WO | 99/50461 A1 | 10/1999 |
| WO | 00/53635 A1 | 9/2000 |

OTHER PUBLICATIONS

International Search Report (Application No. PCT/US2003/036557 Filed Nov. 14, 2003).
Arenberg, D., et al., "Inhibition of Interleukin-8 Reduces Tumorigenesis of Human Non-Small Cell Lung Cancer in SCID Mice", J Clin Invest, vol. 97, pp. 2792-2802 (1996).

*Primary Examiner* — Misook Yu
*Assistant Examiner* — Mark Halvorson
(74) *Attorney, Agent, or Firm* — Ping Wang; Andrews Kurth, LLP

(57) ABSTRACT

The present invention provides a means of inhibiting the growth and metastasis of cancer cells by administering anti-chemokine antibodies. It is possible to identify the particular chemokines which are over-expressed in the tumor using methods of the invention and administer antibodies against that over-expressed chemokine.

19 Claims, No Drawings

ANTI-CHEMOKINE AND ASSOCIATED RECEPTORS ANTIBODIES FOR INHIBITION OF GROWTH OF NEOPLASMS

This application is a continuation application of U.S. patent aplication Ser. No. 10/712,398, filed on Nov. 14, 2003, which claims priority from U.S. Provisional Patent Application 60/426,347, filed on Nov. 15, 2002. The entirety of all of the aforementioned applications is incorporated herein by reference.

This work was partially supported by the United States government, which has certain rights in the invention.

FIELD

This invention relates to antibodies or the use of antibodies directed against certain chemokines. The antibodies block high affinity interactions leading to the growth or migration of cancer cells.

BACKGROUND

Despite recent advances in cancer research, the development of cell-specific therapies for treatment of malignancies remain elusive. The many and complex factors which enable malignant cells to undergo mutations, evade immune protection and promote angiogenesis to deliver nutrients to the rapidly growing cells complicate the development of targeted treatment modalities. Current therapies have multiple untoward side effects. For example, chemotherapy results in multiple painful and sometimes lethal side effects. Advances in biotechnology have promoted the development of targeted biologicals with fewer side effects.

Host cells have surface receptors that associate with ligands to signal and cause host cell activities. The epidermal growth factor receptor helps control cell growth and metastasis. Many tumor cells express higher numbers of epidermal growth factor receptors than normal cells. A new treatment designated IMC-225 was specifically designed to target and block epidermal growth factor receptors preventing cell division and repair. Recently, trastuzumab, which is a HER-2-specific monoclonal antibody, has proven effective at treating metastatic breast cancers. This antibody blocks interactions on cancer cells that inhibit cell growth. Unfortunately, HER-2 is only found on about 25 to 30 percent of breast cancer cells.

A variety of pathogens or toxins activate macrophages, neutrophils, T cells, B cells, monocytes, NK cells, Paneth and crypt cells, as well as epithelial cells shortly after entry into the mucosa. Chemokines are a superfamily of small, cytokine-like proteins that are resistant to hydrolysis, promote neovascularization or endothelial cell growth inhibition, induce cytoskeletal rearrangement, activate or inactivate lymphocytes, and mediate chemotaxis through interactions with G-protein-coupled receptors. Chemokines can mediate the growth and migration of host cells that express their receptors. The cellular mechanisms responsible for the function of the chemokines are often, but not always, $Ca^{2+}$ flux dependent and pertussis toxin-sensitive. However, the precise mechanisms for chemokine-mediated events are not known

SUMMARY

The present invention provides a means of inhibiting the growth and metastasis of cancer cells by administering anti-chemokine antibodies. Exemplified are anti-CXCR1, -CXCR2, -CXCL1, -CXCL2, -CXCL3, -CXCL5, -CXCL6 -CXCL7, -CXCL8, -CXCL12, -CXCR5a, -CXCR5b, -CXCL13, -CXCR6, -CXCL16, -CCL16, -CCL25, -CCL25-1, -CCL25-2, -CX3CR1, and -CX3CL1 antibodies. The invention relates to an antibody or functional fragment thereof that bind to CXCR1, CXCR2, CXCL1, CXCL2, CXCL3, CXCL5, CXCL6 CXCL7, CXCL8, CXCL12, CXCR5a, CXCR5b, CXCL13, CXCR6, CXCL16, CCL16, CCL25, CCL25-1, CCL25-2, CX3CR1, and CX3CL1. This invention utilizes antibodies or antigen-binding fragment(s) that bind to epitope(s) or peptide(s) that consists of 10 to 15 amino acids from Sequences 1 through 22. The antibodies or antigen-binding fragment(s) can be isolated from the serum of immunized hosts, an immortalized cell lines or tissues such as hybridomas, lymphoblastoid or cells generated by methods of recombinant molecule biology. For increased effectiveness, antibodies and fragments may be conjugated or linked to other peptides, proteins, nucleic acid sequence, vitamins, complex or simple carbohydrates or other suitable carrier molecules.

Antibodies or antigen-binding fragments with specificity for functional mutant or variant mammalian chemokines are appropriate. These mutations or polymorphisms occur in nature or can be induced by recombinant molecular biological methods to generate single, multiple, or continuous amino acid residues, described in Sequences 1 through 22, that are deleted, added, and/or substituted for other or no amino acids.

The antibodies for use in accord with the teachings of this specification may be administered systemically or mucosally. Mucosal means include oral, intranasal, ocular, intravaginal, rectal and/or intraurethral administration in liquid or particulate form or on solid supports. Systemic means include parenteral means such as intravenous, subcutaneous or intramuscular administration.

DETAILED DESCRIPTION

The invention describes a method of identifying and isolating cancer cells from adenoma, carcinoma, leukemia, lymphoma, melanoma, or myeloma using the antibodies in accord with the teachings of this specification. Also, as demonstrated herein, anti-CXCR1, -CXCR2, -CXCL1, -CXCL2, -CXCL3, -CXCL5, -CXCL6 -CXCL7, -CXCL8,-CXCL12, -CXCR5a, -CXCR5b, -CXCL13, -CXCR6, -CXCL16, -CCL16, -CCL25, -CCL25-1, -CCL25-2, -CX3CR1, and -CX3CL1 antibodies can to administered to inhibit the rate of growth, metastasis and/or angiogenesis mediated by adenomas, carcinomas, leukemias, lymphomas, melanomas, and/or myelomas.

Materials and Methods

Primer Design

Messenger RNA sequences for CXCR1, CXCR2, CXCL1, CXCL2, CXCL3, CXCL5, CXCL6 CXCL7, CXCL8, CXCL12, CXCR5a, CXCR5b, CXCL13, CXCR6, CXCL16, CCL16,CCL25, CCL25-1, CCL25-2, CX3CR1, and CX3CL1 were obtained from the NIH -NCBI gene bank database (Sequences 23 through 44). Primers were designed using the BeaconJ 2.0 computer program. Thermodynamic analysis of the primers was conducted using computer programs: Primer Premier) and MIT Primer 3. The resulting primer sets were compared against the entire human genome to confirm specificity.

Real Time PCR Analysis

Cancer cell lines (ATCC, Rockville, Md.) were cultured in RMPI-1640 containing 10% fetal calf serum supplemented with non-essential amino acids, L-glutamate, and sodium pyruvate (complete media). Primary tumor and normal-paired matched tissues were obtained from clinical isolates (Clinomics Biosciences, Frederick, Md. and UAB Tissue Procurement, Birmingham, Ala.). Messenger RNA (mRNA) was isolated from $10^6$ cells using TriReagent (Molecular Research Center, Cincinnati, Ohio) according to manufacturer's protocols. Potential genomic DNA contamination was removed from these samples by treatment with 10 U/F1 of RNase free DNase (Invitrogen, San Diego, Calif) for 15 minutes at 37° C. RNA was then precipitated and resuspended in RNA Secure (Ambion, Austin, Tex.). The cDNA was generated by reverse transcribing approximately 2 μg of total RNA using Taqman7 reverse transcription reagents (Applied-Biosystems, Foster City, Calif.) according to manufacturer's protocols. Subsequently, cDNA's were amplified with specific human cDNA primers, to CXCR1, CXCR2, CXCL1, CXCL2, CXCL3, CXCL5, CXCL6 CXCL7, CXCL8, CXCL12, CXCR5a, CXCR5b, CXCL13, CXCR6, CXCL16, CCL16, CCL25, CCL25-1, CCL25-2, CX3CR1, and CX3CL1, using SYBR7 Green PCR master mix reagents (Applied Biosystems) according to manufacturer's protocol. The level of copies of mRNA of these targets were evaluated by real-time PCR analysis using the BioRad Icycler and software (Hercules, Calif.).

Anti-sera Preparation

The 15 amino acid peptides from CXCR1, CXCR2, CXCL1, CXCL2, CXCL3, CXCL5, CXCL6 CXCL7, CXCL8, CXCL12, CXCR5a, CXCR5b, CXCL13, CXCR6, CXCL16, CCL16, CCL25, CCL25-1, CCL25-2, CX3CR1, and CX3CL1 (Sequences 1 through 22) were synthesized (Sigma Genosys, The Woodlands, Tex.) and conjugated to hen egg lysozyme (Pierce, Rockford, Ill.) to generate the "antigen" for subsequent immunizations for anti-sera preparation or monoclonal antibody generation. The endotoxin levels of chemokine peptide conjugates were quantified by the chromogenic Limulus amebocyte lysate assay (Cape Cod, Inc., Falmouth, Mass.) and shown to be <5 EU/mg. 100 μg of the antigen was used as the immunogen together with complete Freund's adjuvant Ribi Adjuvant system (RAS) for the first immunization in a final volume of 1.0 ml. This mixture was administered in 100 ml aliquots on two sites of the back of the rabbit subcutaneously and 400 ml intramuscularly in each hind leg muscle. Three to four weeks later, rabbits received 100 μg of the antigen in addition to incomplete Freund's adjuvant for 3 subsequent immunizations. Anti-sera were collected when anti -CXCR1, -CXCR2, -CXCL1, -CXCL2, -CXCL3, -CXCL5, -CXCL6 -CXCL7, -CXCL8, -CXCL12, -CXCR5a, -CXCR5b, -CXCL13, -CXCR6, -CXCL16, -CCL16, -CCL25, -CCL25-1, -CCL25-2, -CX3CR1, and -CX3CL1 antibody titers reached 1:1,000,000. Subsequently, normal or anti-sera were heat-inactivated and diluted 1:50 in PBS.

Monoclonal Antibody Preparation

The 15 amino acid peptides from CXCR1, CXCR2, CXCL1, CXCL2, CXCL3, CXCL5, CXCL6 CXCL7, CXCL8, CXCL12, CXCR5a, CXCR5b, CXCL13, CXCR6, CXCL16, CCL16, CCL25, CCL25-1, CCL25-2, CX3CR1, and CX3CL1 (Sequences 1 through 22) were synthesized (Sigma Genosys) and conjugated to hen egg lysozyme (Pierce) to generate the "antigen" for subsequent immunizations for anti-sera preparation or monoclonal antibody generation. The endotoxin levels of chemokine peptide conjugates were quantified by the chromogenic Limulus amebocyte lysate assay (Cape Cod, Inc., Falmouth, Mass.) and shown to be <5 EU/mg. 100 μg of the antigen was used as the immunogen together with complete Freund's adjuvant Ribi Adjuvant system (RAS) for the first immunization in a final volume of 200 μl. This mixture was subcutaneously administered in 100 μl aliquots at two sites of the back of a rat, mouse, or immunoglobulin-humanized mouse. Two weeks later, animals received 100 μg of the antigen in addition to incomplete Freund's adjuvant for 3 subsequent immunizations. Serum were collected and when anti-CXCR1, -CXCR2, -CXCL1, -CXCL2, -CXCL3, -CXCL5, -CXCL6 -CXCL7, -CXCL8, -CXCL12, -CXCR5a, -CXCR5b, -CXCL13, -CXCR6, -CXCL16, -CCL16, -CCL25, -CCL25-1, -CCL25-2, -CX3CR1, or -CX3CL1 antibody titers reached 1:2,000,000, hosts were sacrificed and splenocytes were isolated for hybridoma generation. Briefly, B cells from the spleen or lymph nodes of immunized hosts were fused with immortal myeloma cell lines (e.g., YB2/0). Hybridomas were next isolated after selective culturing conditions (i.e., HAT-supplemented media) and limiting dilution methods of hybridoma cloning. Cells that produce antibodies with the desired specificity were selected using ELISA. Hybridomas from normal rats or mice were humanized with molecular biological techniques in common use. After cloning a high affinity and prolific hybridoma, antibodies were isolated from ascites or culture supernatants and adjusted to a titer of 1:2,000,000 and diluted 1:50 in PBS.

Anti-sera or Monoclonal Antibody Treatment

The NIH-III mice (8 to 12 weeks old, Charles River Laboratory, Wilmington, Mass.), which lack T, B, and NK cells, received $1 \times 10^6$ cancer cells, subcutaneously, for the establishment of a tumor. Correspondingly, freshly isolated or liquid nitrogen frozen 1 g of tumor tissue were surgically implanted in the intestinal adipose tissue for the generation of tumor. Once the xenografted tumor growth reached 5 mm in size the NIH-III mice received 200 .mu.1 intraperitoneal injections of either antisera or monoclonal antibodies every three days and the tumor was monitored for progression or regression of growth.

Data Analysis

SigmaStat 2000 (Chicago, Ill.) software was used to analyze and confirm the statistical significance of data. The data were subsequently analyzed by the Student's t-test, using a two-factor, unpaired test. In this analysis, treated samples were compared to untreated controls. The significance level was set at $p<0.05$.

Results

Semiquantitative RT-PCR Identification of Molecular Targets

The RT-PCR products obtained using CXCR1-, CXCR2-, CXCL1-, CXCL2-, CXCL3-, CXCL5-, CXCL6-, CXCL7-, CXCL8-, CXCL12-, CXCR5a-, CXCR5b-, CXCL13-, CXCR6-, CXCL16-, CCL16-, CCL25-, CCL25-1-, CCL25-2-, CX3CR1-, or CX3CL1- specific primer sets did not cross react with other gene targets due to exclusion of primers that annealed to host sequences (NIH-NCBI Genebank). The primers used produced different size amplicon products relative the polymorphisms that resulted in CXCR5a versus CXCR5b and CCL25, CCL25-1, versus CCL25-2. To this end, RT-PCR analysis of adenoma, carcinoma, leukemia, lymphoma, melanoma, and/or myeloma cell lines and tumor tissue revealed that CXCR1, CXCR2, CXCL1, CXCL2, CXCL3, CXCL5, CXCL6 CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, and CX3CL1 were differentially expressed by cancer cells.

In vitro Growth Studies

The adenoma, carcinoma, leukemia, lymphoma, melanoma, and/or myeloma cell lines were grown in complete media in the presence or absence of antibodies specific for CXCR1, CXCR2, CXCL1, CXCL2, CXCL3, CXCL5, CXCL6 CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, or CX3CL1. The growth of cancer cell lines expressing CXCR1 and/or CXCR2 were inhibited by antibodies to CXCR1, CXCR2, CXCL1, CXCL2, CXCL3, CXCL5, CXCL6 CXCL7, or CXCL8. Similarly, the growth of cancer cell lines expressing CXCR4 were inhibited by antibodies to CXCR4 or CXCL12. The growth of cancer cell lines expressing CXCR5a or CXCR5a were inhibited by antibodies to CXCR5a, CXCR5b, or CXCL13. The proliferation of cancer cell lines expressing CXCR6 or were inhibited by antibodies to CXCR6 or CXCL16. The growth of cancer cell lines expressing CCR9 were inhibited by antibodies to CCR9 or CCL25, CCL25-1, and CCL25-2. The propagation of cancer cell lines expressing CX3CR1 were inhibited by antibodies to CX3CR1 or CX3CL1. Of interest, antibodies against the soluble ligands, CXCL1, CXCL2, CXCL3, CXCL5, CXCL6, CXCL7, CXCL8, CXCL12, CXCL13, CXCL16, CCL16, CCL25, CCL25-1, CCL25-2, or CX3CL1, were more effective at growth inhibition that those directed against the membrane receptors.

In vitro Angiogenesis Studies

The microvascular endothelial cells (Cell Systems, Wirkland, Wash.) were grown according to manufacturer's protocols and allowed to form microvascular venules in an in vitro assay for angiogenesis (BD-Biocoat, Hercules, in the presence or absence of antibodies specific for CXCR1, CXCR2, CXCL1, CXCL2, CXCL3, CXCL5, CXCL6 CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, or CX3CL1. The angiogenesis was inhibited by antibodies against CXCR1, CXCR2, CXCL1, CXCL2, CXCL3, CXCL5, CXCL6 CXCL7, CXCL8, CXCR4, CXCL12, CXCR6 or CXCL16.

In vivo Growth Studies

Cancer cell lines or primary tumor tissue were adoptively transferred into NIH-III mice and allowed to form the xenograft tumor of interest. Antibodies directed against CXCR1, CXCR2, CXCL1, CXCL2, CXCL3, CXCL5, CXCL6 CXCL7, CXCL8, CXCR4, CXCL12, CXCR5a, CXCR5b, CXCL13, CXCR6, CXCL16, CCL16, CCR9, CCL25, CCL25-1, CCL25-2; CX3CR1, or CX3CL1 differentially affected the progression and regression of tumor size. In certain cases, antibodies directed towards CXCR1, CXCR2, CXCL1, CXCL2, CXCL3, CXCL5, CXCL6 CXCL7, CXCL8, CXCR4, CXCL12, CXCR6 or CXCL16 effectively lead to the both regression and impeding progression of tumor growth. Antibodies directed against CXCR4, CXCL12, CXCR5a, CXCR5b, CXCL13, CCL16, CCR9, CCL25, CCL25-1, CCL25-2, CX3CR1, or CX3CL1 were effective at inhibiting the progression of tumor size.

The protein sequences of the chemokines used herein are recorded in NIH-NCBI Genebank as: (1) CXCR1 (ACCESSION# NM 000634), (2) CXCR2(ACCESSION# NM 001557), (3) CXCL1 (ACCESSION# NM_001511), (4) CXCL2 (ACCESSION# NM_001557), (5) CXCL3 (ACCESSION# NM_002090), (6) CXCL5 (ACCESSION# NM_002994), (7) CXCL6 (ACCESSION# NM_002993), (8) CXCL7 (ACCESS1ON# NM_002704),(9) CXCL8 (ACCESSION# XM_170504), (10) CXCR4 (ACCESSION# NM_003467), (11) CXCL12 (ACCESSION# NM_000609), (12) CXCR5A (ACCESSION# NM_032966), (13) CXCR5B (ACCESSION# NM_001716), (14) CXCL13 (ACCESSION# NM_006419), (15) CXCR6 (ACCESSION# NM_006564), (16) CXCL16 (ACCESSION# NM022059), (17) CCL16 (ACCESSION# NM_004590), (18) CCL25 (ACCESSION# 015444), (19) CCL25-1 (ACCESSION# NM_005624), (20) CCL25-2 (ACCESSION# NM_148888), (21) CX3CR1 (ACCESSION# NM_001337), and (22) CX3CL1 (ACCESSION# NM_002996).

The cDNA sequences are known and are available in NIH-NCBI Genebank under the following accession numbers: (23) CXCR1 (ACCESSION# NM 000634), (24) CXCR2 (ACCESSION# NM_001557), (25) CXCL1 (ACCESSION# NM_001511). (26) CXCL2 (ACCESSION# NM_001557), (27) CXCL3 (ACCESSION# NM_002090), (28) CXCL5 (ACCESSION# NM_002994), (29) CXCL6 (ACCESSION# NM_002993), (30) CXCL7 (ACCESSION# NM_002704), (31) CXCL8 (ACCESSION# XM_170504), (32) CXCR4 (ACCESSION# NM_003467), (33) CXCL12 (ACCESSION# NM_000609), (34) CXCR5A (ACCESSION# NM_032966), (35) CXCR5B (ACCESSION# NM_001716) (36) CXCL13 (ACCESSION# NM_006419), (37) CXCR6 (ACCESSION# NM_006564), (38) CXCL16 (ACCESSION# NM_022059), (39) CCL16 (ACCESSION# NM_004590), (40) CCL25 (ACCESSION# 015444), (41) CCL25-1 (ACCESSION# NM_005624), (42) CCL25-2 (ACCESSION# NM_148888), (43) CX3CR1 (ACCESSION# NM_001337), and (44) CX3CL1 (ACCESSION# NM_002996).

As shown in the table below, the particular chemokines which are most which any tumor expresses may vary. It is possible, using methods of the invention, to customize treatment for the particular patient, depending on the chemokines over-expressed by the patient's own tumor. It is possible to identify the particular chemokines which are over-expressed in the tumor using methods of the invention and administer antibodies against that over-expressed chemokine. The tailoring of treatment for the cancer patient is novel, and is a particularly valuable aspect of the invention.

The method consists of 1) exposing samples of malignant tissue or products therefrom to an array of antibodies to different chemokines, allowing the antibodies to bind to the malignant tissue, then measure the amount of the chemokines by measuring the amount of chemokine bound to particular antibodies to identify the level of expression of each chemokine. The patient is then given the antibodies against the over-expressed chemokine(s). However, the level of each chemokine may also be evaluated using PCR technologies. Such direct evaluation is now easily done, as shown above. See particularly the section entitled, "Semiquantitative RT-PCR identification of molecular targets".

Antibodies of the invention can be administered in the usually accepted pharmaceutically acceptable carriers. For example, compositions containing antibodies can be prepared in accord with the section entitled "Monoclonal antibody preparation". Acceptable carriers include, but are not limited to, saline, buffered saline, glucose in saline. Solid supports, liposomes or microspheres may also be used as carriers for administration of the antibodies. Antibodies of the invention may be administered directly to target tissue. For example, compositions containing the compositions containing antibodies as prepared under the heading "anti-sera preparation" can be administered intravenously, rectally vaginally, intrathecally, by inhalation, transvaginally, transurethrally or directly to tissue during surgery. The anti-sera preparations may also be placed on a solid support such as a sponge or gauze for administration of antibodies against the target chemokine to the affected tissues, including administration directly to the tumor bed during invasive procedures. The table on the following page indicates the differing amounts of particular chemokines over-expressed in particular tumors that were studied.

TABLE I

Chemokine, Chemokine Receptor and Cancer Association (dependent of stage of disease)

| Cancer | Chemokine | Chemokine Receptor |
| --- | --- | --- |
| Carcinoma | CCL1, CCL4, CCL17, CCL19, CCL21, CCL22, CCL25 | CCR7, CCR8, CCR9 |
|  | CXCL12, CXCL13, CXCL16 | CXCR4, CXCR5, CXCR6, CX3CR1 |
| Leukemia | CCL1, CCL4, CCL17, CCL19, CCL21, CCL22, CCL25 | CCR7, CCR8, CCR9 |
|  | CXCL12 | CXCR4 |
| Lymphoma | CXCL12, CXCL13 | CXCR4, CXCR5 |
| Melanoma | CCL25, CCL27 | CCR9, CCR10 |
|  | CXCL1, CXCL2, CXCL3, CXCL5, CXCL6, CXCL7, CXCL8, CXCL12, CXCL13, CXCL16 | CXCR1, CXCR2, CXCR4, CXCR5, CXCR6 |
|  | CX3CL1 | CX3CR1 |
| Sarcoma | CCL1, CCL3, CCL4, CCL5, CCL7, CCL8, CCL11, CCL13, CCL17, CCL22, CCL24 | CCR3, CCR5, CCR8 |
|  | CXCL12 | CXCR4 |
|  | CX3CL1 | CX3CR1 |

Dosage would more commonly be in the range of 0.01 to 1000 mg/kg/da, more often in the range of 0.1 to 100 mg/kg/da. As expected, the dosage will be dependant on the condition, size, age and condition of the patient.

What is claimed is:

1. A method of inhibiting melanoma cell migration in a host, comprising:
    administering into said host a migration-inhibiting effective amount of a composition comprising:
    (1) an anti-CXCL-13 antibody, an antigen-binding antibody fragment of an anti-CXCL-13 antibody, an anti-CXCR5 antibody, or an antigen-binding antibody fragment of an anti-CXCR5 antibody; and
    (2) a pharmaceutically acceptable carrier,
    wherein said composition is administered directly to tumor tissue.

2. The method of claim 1, wherein said anti-CXCL-13 antibody or said anti-CXCR5 antibody is a human antibody.

3. The method of claim 1, wherein said anti-CXCL-13 antibody or said anti-CXCR5 antibody is a humanized antibody.

4. The method of claim 1, wherein said anti-CXCL-13 antibody or said anti-CXCR5 antibody is a chimeric antibody.

5. The method of claim 1, wherein said composition comprises both said anti-CXCL-13 antibody and said anti-CXCR5 antibody.

6. The method of claim 1, wherein said pharmaceutically acceptable carrier comprises a solid support.

7. The method of claim 6, wherein said solid support is a sponge or gauze.

8. The method of claim 1, wherein said pharmaceutically acceptable carrier comprises liposomes.

9. The method of claim 1, wherein said pharmaceutically acceptable carrier comprises microspheres.

10. The method of claim 1, wherein said antibody is administered directly to tumor bed during an invasive procedure.

11. The method of claim 1, wherein said anti-CXCL-13 antibody, said antigen-binding antibody fragment of said anti-CXCL-13 antibody, said anti-CXCR5 antibody, or said antigen-binding antibody fragment of said anti-CXCR5 antibody is administered at a dose range of 0.01-1000 mg/kg/day.

12. The method of claim 1, wherein said anti-CXCL-13 antibody or said anti-CXCR5 antibody is administered at a dose range of 0.1-100 mg/kg/day.

13. The method of claim 1, wherein said pharmaceutically acceptable carrier is saline.

14. The method of claim 13, wherein said saline is buffered saline.

15. The method of claim 1, wherein said pharmaceutically acceptable carrier is glucose in saline.

16. The method of claim 1, wherein said composition further comprises an antibody, or an antigen-binding antibody fragment, that binds to a chemokine or chemokine receptor selected from the group consisting of CCL25, CCL27, CXCL1, CXCL2, CXCL3, CXCL5, CXCL6, CXCL7, CXCL8, CXCL12 CXCL16, CX3CL1, CCR9, CCR10, CX3CR1 CXCR1, CXCR2, CXCR4, CXCR6, CX3CR1.

17. A method of inhibiting melanoma cell growth in a host, comprising:
    administering into said host a growth-inhibiting effective amount of a composition comprising:
    (1) an anti-CXCL-13 antibody, an antigen-binding antibody fragment of an anti-CXCL-13 antibody, an anti-CXCR5 antibody, or an antigen-binding antibody fragment of an anti-CXCR5 antibody; and
    (2) a pharmaceutically acceptable carrier.

18. The method of claim 17, wherein said composition comprises
    (1) an anti-CXCL-13 antibody or an antigen-binding antibody fragment of an anti-CXCL-13 antibody;
    (2) an anti-CXCR5 antibody or an antigen-binding antibody fragment of an anti-CXCR5 antibody; and
    (3) a pharmaceutically acceptable carrier.

19. The method of claim 17, wherein said composition further comprises an antibody, or an antgen-binding antibody fragment, that binds to a chemokine or chemokine receptor selected from the group consisting of CCL25, CCL27, CXCL1, CXCL2, CXCL3, CXCL5, CXCL6, CXCL7, CXCL8, CXCL12 CXCL16, CX3CL1, CCR9, CCR10, CX3CR1 CXCR1, CXCR2, CXCR4, CXCR6, CX3CR1.

* * * * *